United States Patent [19]

Siegel

[11] Patent Number: 4,803,983

[45] Date of Patent: Feb. 14, 1989

[54] MUSCLE BIOPSY CLAMP

[76] Inventor: Irwin M. Siegel, 1404 Forest Ave., Evanston, Ill. 60201

[21] Appl. No.: 195,429

[22] Filed: May 13, 1988

Related U.S. Application Data

[63] Continuation of Ser. No. 029,068, Mar. 23, 1987, abandoned.

[51] Int. Cl.$^4$ .............................................. A61B 17/28
[52] U.S. Cl. .................................... 128/321; 128/346; 128/749
[58] Field of Search ............... 128/321, 322, 346, 751, 128/749

[56] References Cited

U.S. PATENT DOCUMENTS 4,226,240 10/1980 Walker ................................. 128/321
4,651,737 3/1987 Deniega ........................... 128/346 X

FOREIGN PATENT DOCUMENTS 401732 9/1909 France ................................. 128/321
1291800 10/1972 United Kingdom ................ 128/322

OTHER PUBLICATIONS

American V. Mueller catalog, p. 104 (1980).

Primary Examiner—Michael H. Thaler
Attorney, Agent, or Firm—Dressler, Goldsmith, Shore, Sutker & Milnamow, Ltd.

[57] ABSTRACT

A muscle biopsy clamp operable with one hand to securely grip and retain an excised specimen in unstressed condition. The clamping jaws are in the form of two-pronged forks lying in a plane transverse to the major plane of the instrument which includes the straight handle members, the looped finger grips and ratchet locking members between the handle members. The jaws are also angled approximately 30° with respect to the straight handle members to provide optimum visualization and maneuverability. Weakened areas are formed in the handle members permitting the finger grips to be snapped off without disturbing a gripped excised specimen so that the specimen can be placed in standard specimen jars for laboratory analysis.

4 Claims, 2 Drawing Sheets

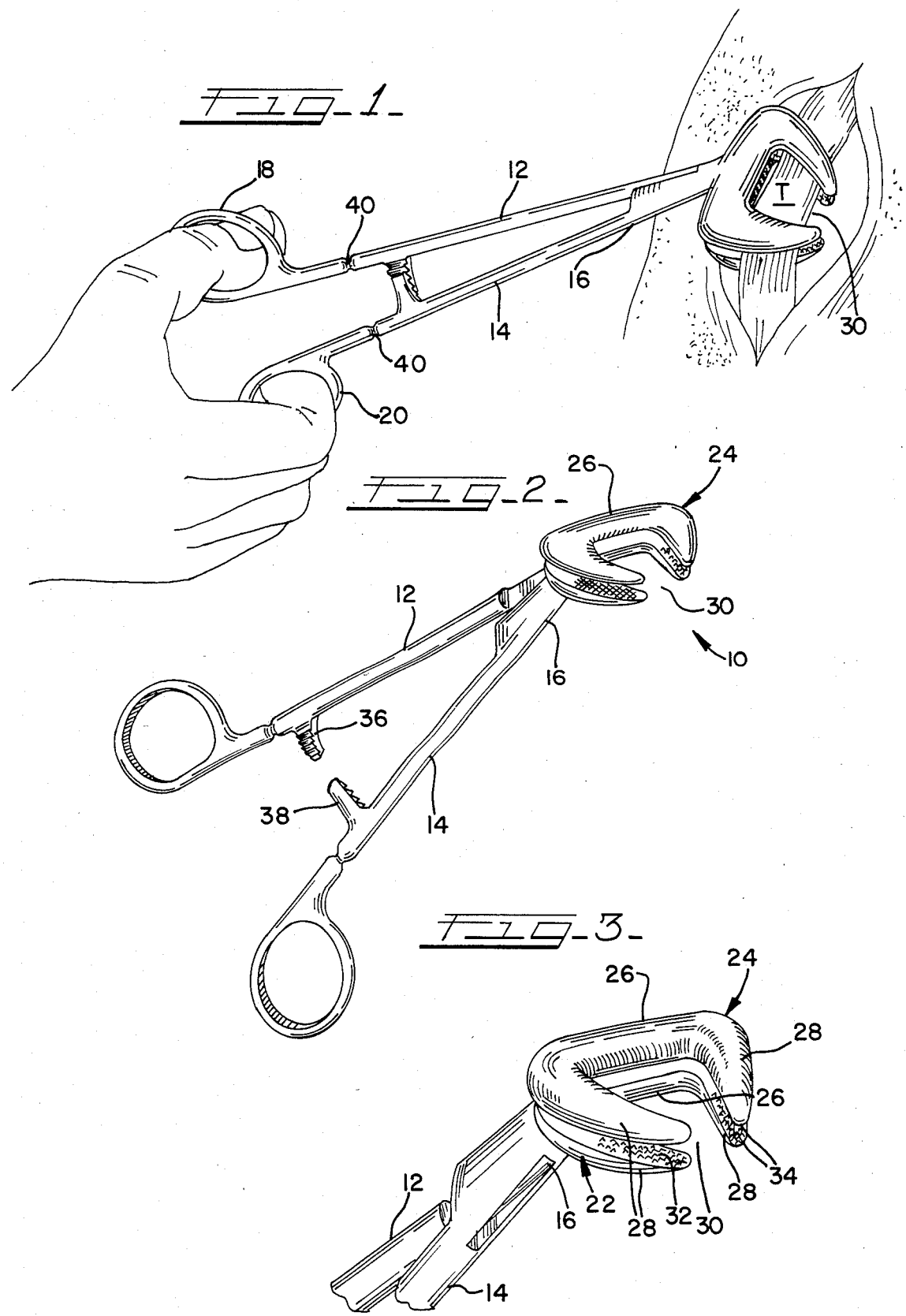

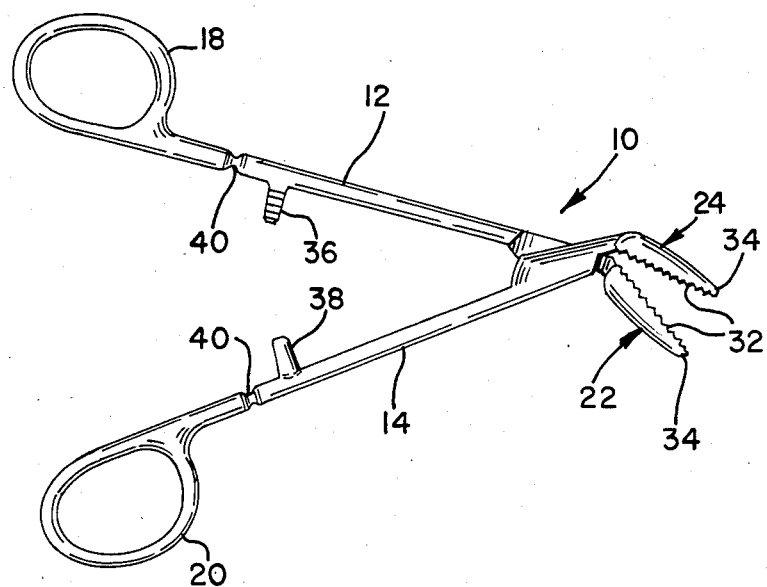
FIG-4-
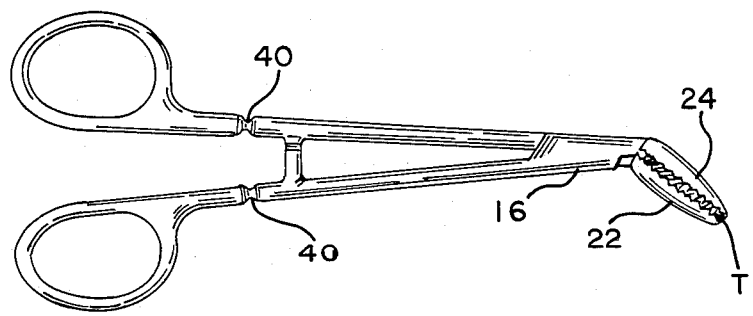
FIG-5-
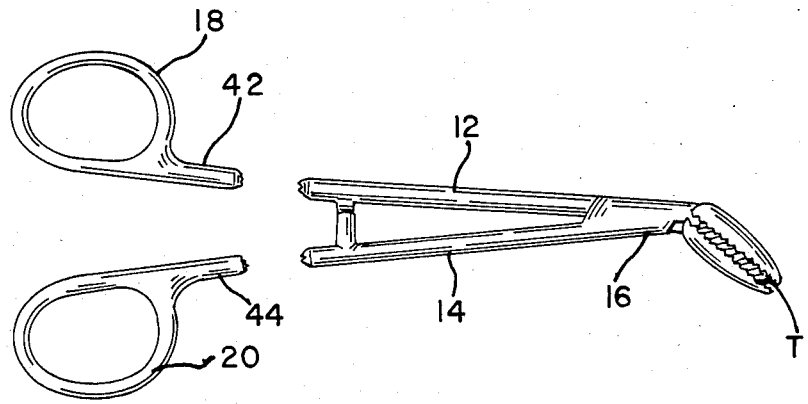
FIG-6-

MUSCLE BIOPSY CLAMP

This application is a continuation of application Ser. No. 029,068, filed Mar. 23, 1987, now abandoned.

TECHNICAL FIELD

This invention relates to medical surgical instruments and, more particularly, to a surgical clamp for defining and retaining a tissue sample suitable for histological evaluation.

BACKGROUND OF THE INVENTION

Biopsy specimens of muscle fiber and other tissue have heretofore been obtained with a variety of clamping and/or cutting instruments. For example, U.S. Pat. Nos. 2,778,357 and 3,353,531 show instruments which, in effect, punch out and retain a tissue specimen. Instruments of that type are best suited for obtaining relatively small tissue specimens from body cavities, or the like, but are not suitable for histologic examination of muscle tissue.

Biopsy of muscle for histopathological evaluation requires that the tissue be clamped at the time of excision to prevent contraction which causes microscopic artifacts. To this end, biopsy instruments have heretofore been provided using various clamping techniques to fix muscle from which the pathologist can cut well oriented longitudinal and cross sections. However, none of the clamps of this type is wholly satisfactory for reasons of design or fabrication.

A commonly used biopsy clamp is known as the Rayport clamp and is described in U.S. Pat. No. 3,687,131. The Rayport clamp comprises a hinged structure which requires the use of two hands and a separate hemostat clamp to achieve the required clamping action. The patented clamp is also somewhat cumbersome and difficult to apply in certain body areas because of its particular uni-planar design and laterally projecting handle. Another biopsy muscle clamp in common use is known as the Price clamp and comprises a stainless steel tweezers-like structure having forked ends for isolating and gripping the muscle tissue. The Price clamp is likewise disadvantageously uni-planar and also requires sterilization and re-use because of its relatively expensive construction.

There thus exists a need for a biopsy clamp which is simple and certain in its application, which requires only one hand for its use and which will grip the biopsy tissue firmly enough to prevent shortening disfiguring contraction. The instrument should be sized to fit into a standard specimen jar for convenience of handling. Preferably, the clamp should be disposable for cost-effectiveness and convenience, thereby eliminating the need for its return from the laboratory to the operating room.

SUMMARY OF THE INVENTION

The present invention provides an improved muscle biopsy clamp which is easily and efficiently operable with one hand and substantially eliminates the disadvantages encountered with prior clamps.

Briefly, the invention comprises a pair of elongated, hingedly connected handle members having looped finger grips at one end thereof. At the opposite end, and in close proximity to the hinged connection, the handle members comprise a pair of opposed clamping jaw members. The jaw members are fork-shaped with the ends of the prongs converging slightly toward each other. Mating surfaces of the jaw members are formed with gripping serrations, and the members are oriented transversely of, and angled from, the handle members to provide the surgeon with optimum unobstructed vision and ease of access to body muscle.

Opposed ratchet members are integrally formed on the handle members and project inwardly therefrom toward each other. The ratchet members cooperate to lock the jaws and securely clamp therein the muscle tissue to be dissected. Retention of the tissue sample in its original state is thereby assured.

The handle members are provided with self-contained break-away means between the finger grips and the ratchet. As a result, the finger grips may be readily snapped off and the remainder of the instrument, with the specimen securely gripped therein, may be inserted into a standard specimen jar for the pathological analysis. The entire instrument is moldable from suitable plastics so that the same is discardable after a single use and need not be sterilized for return to the operating room.

Numerous other advantages and features of the present invention will become readily apparent from the following detailed description of a preferred embodiment thereof, from the claims, and from the accompanying drawings.

BRIEF DESCRIPTION OF THE DRAWINGS

In the accompanying drawings forming a part of the specification, and in which like numerals are employed to designate like parts throughout the same, FIG. 1 is a perspective view of a biopsy clamp embodying the principles of the invention and showing the same in use and clamping a specimen;

FIG. 2 is a perspective view of the open clamp;

FIG. 3 is an enlarged perspective view of the jaw portion of the clamp;

FIG. 4 is an elevational view of the open clamp;

FIG. 5 is a similar view with the jaws locked and a muscle specimen retained therein; and FIG. 6 is a similar view illustrating the finger grip portion broken away.

DETAILED DESCRIPTION OF THE INVENTION

Referring in greater detail to the various figures of the drawings, it will be seen that the reference numeral 10 indicates generally a muscle biopsy clamp embodying the principles of the invention. Clamp, 20 comprises a pair of elongated handle members 12 and 14 hingedly connected together in scissors-fashion at 16. At their rear ends, the handle members 12 and 14 are provided with looped finger grips 18 and 20. As illustrated, the handle members and finger grips lie in a single vertical plane, namely, the drawings sheet of FIGS. 4–6.

At their front ends, and closely adjacent the hinge 16, the handle members 12 and 14 comprise opposed jaw members 22 and 24. Each of the jaw members 22 and 24 comprises a fork-like structure 26 having a pair a prongs 28,28, which converge slightly toward each other at the bottom end 30 of the forked structure. The inner faces of the prongs 28 are formed with mating serrations 32, while the outer surfaces of said prongs taper smoothly into reduced dimension front tips 34. The jaw members 22 and 24 lie in a plane substantially perpendicular to the plane of handle members 12 and 14 and also are angled with relation to the straight handle members.

Preferably, the angle between the handle members and jaw members is approximately 30°, which has been found to provide optimum visualization and ease of manipulation under varying conditions of use.

Medially of their length, the handle members 12 and 14 have integrally formed ratchet members 36 and 38 positioned in opposed relationship and adapted to function in a conventional manner. Each of the handle members 12 and 14 is likewise formed with a reduced diameter, preferentially weakened area 40 positioned behind the ratchet members 36 and 38 and between said members and the finger grips 18 and 20.

Operation of the clamp 10 should now be readily understandable without further description. Using the thumb and a finger of only one hand, the surgeon is able to dissect and isolate the desired tissue section T between the jaw members 22 and 24, being aided in this operation by the angle of said jaw members and the smoothly probing tips 34 thereof. When properly positioned, the surgeon simply applies finger pressure to lock the ratchet members 36 and 38 and thereby securely grip the specimen between the jaw members. The tissue section may then be dissected with the other hand by cutting around the outside of the prongs 28 in a conventional manner. When the clamp is removed with the tissue section, the finger grips 18 and 20 may be easily snapped off, or cut off, together with handle segments 42 and 44, and the specimen and the reduced size gripping portions of the clamp conveniently placed in a standard specimen jar for uncontaminated removal to the laboratory.

As indicated, the entire clamp 10 preferably is molded of suitable plastics, such as, high-density polyethylene or talc-filled polypropylene. Thus, the relatively inexpensive instrument may be discarded after a single use.

It will be readily observed from the foregoing detailed description of the invention and the illustrative embodiment thereof that numerous variations and modifications may be effected by those skilled in the art without departing from the true spirit and scope of the novel concept of the principles of the invention.

What is claimed is:

1. A muscle biopsy clamp comprising:
   a pair of elongated mutually hinged handle members;
   finger grip means of one end of said handle members, said handle members and finger grip means extending in a common plane containing a hinge; and
   opposed jaw members at the opposite end of said handle members, each of which comprises an open-ended two-pronged fork having gripping serrations on its opposed inner faces and cooperable for securely gripping a tissue specimen therebetween such that a portion of the specimen remains in its original state and extending in a plane transverse to said common plane and inclined from said handle members,
   said prongs tapering smoothly and terminating in reduced diameter tips the tips of each jaw member converging toward each other at the open end of the fork.

2. A muscle biopsy clamp according to claim 1 including locking means on said handle members and cooperable for locking said jaw members about a tissue specimen comprising opposed ratchet members projecting inwardly from said handle members and medially of the length thereof, said ratchet members extending in said common plane.

3. A muscle biopsy clamp according to claim 2 including frangible means on said handle means for selectively removing said finger grip means without affecting an excised tissue specimen locked between said jaw members comprising a preferentially weakened area in each of said handle members between said ratchet members and said finger grip means.

4. A muscle biopsy clamp comprising:
   a pair of elongated mutually hinged handle members;
   finger grip means at one end of said handle members, said handle members and finger grip means extending in a common plane containing a hinge;
   opposed jaw members at the opposite end of said handle members and cooperable for securely gripping a tissue specimen therebetween such that a portion of the specimen remains in its original state,
   said jaw members comprising an open-ended two-pronged fork having gripping serrations on the opposed inner faces of said prongs, said forks extending in a plane transverse to said common plane and inclined from the handle member, the angle of inclination between said forks and handle members being approximately 30°,
   said prongs tapering smoothly and terminating in reduced diameter tips, the tips of each jaw member converging toward each other at the open end of the fork;
   locking means on said handle members cooperable for locking said jaw members about a tissue specimen; and
   frangible means on said handle members for selectively removing said finger grip means without affecting an excised tissue specimen locked between said jaw members.

* * * * *